United States Patent [19]

Scheff et al.

[11] Patent Number: 5,172,000
[45] Date of Patent: Dec. 15, 1992

[54] SPATIAL FILTER FOR OPTICALLY BASED DEFECT INSPECTION SYSTEM

[75] Inventors: Victor A. Scheff, Alameda; Lawrence H. Lin, Alamo; Robert B. Howe, San Jose, all of Calif.

[73] Assignee: Insystems, Inc., San Jose, Calif.

[21] Appl. No.: 608,208

[22] Filed: Nov. 2, 1990

[51] Int. Cl.[5] .............................................. G02B 27/42
[52] U.S. Cl. .................................. 250/550; 356/237; 382/31
[58] Field of Search ............... 250/562, 563, 572, 550; 356/71, 237, 239, 294; 382/8, 31

[56] References Cited

U.S. PATENT DOCUMENTS

| | | | |
|---|---|---|---|
| 4,330,775 | 5/1982 | Iwamoto et al. | 356/71 |
| 4,806,774 | 2/1989 | Lin et al. | 250/550 |
| 4,871,257 | 10/1989 | Suzuki et al. | 356/237 |

*Primary Examiner*—David C. Nelms
*Attorney, Agent, or Firm*—Stoel Rives Boley Jones & Grey

[57] ABSTRACT

In an imaging system (10) for detecting defects in a specimen (14) having a repetitive pattern (16), a spatial filter (50) receives a spatial frequency spectrum produced by a Fourier transform lens (34) and blocks preselected spatial frequency components thereof. The spatial filter includes an array of substantially parallel opaque stripes (70a-70c) that are positioned on a substantially transparent substrate (72). In one embodiment, the stripes are spaced apart by equal distances (78) and are of increasing widths (76a-76c) that correspond to the orders of diffraction of the Fourier transform pattern (45) produced by the Fourier transform lens. The spatial filter can be used to filter light spots forming a Fourier transform pattern for specimens having repetitive pattern sizes included within a specified range of sizes.

17 Claims, 4 Drawing Sheets

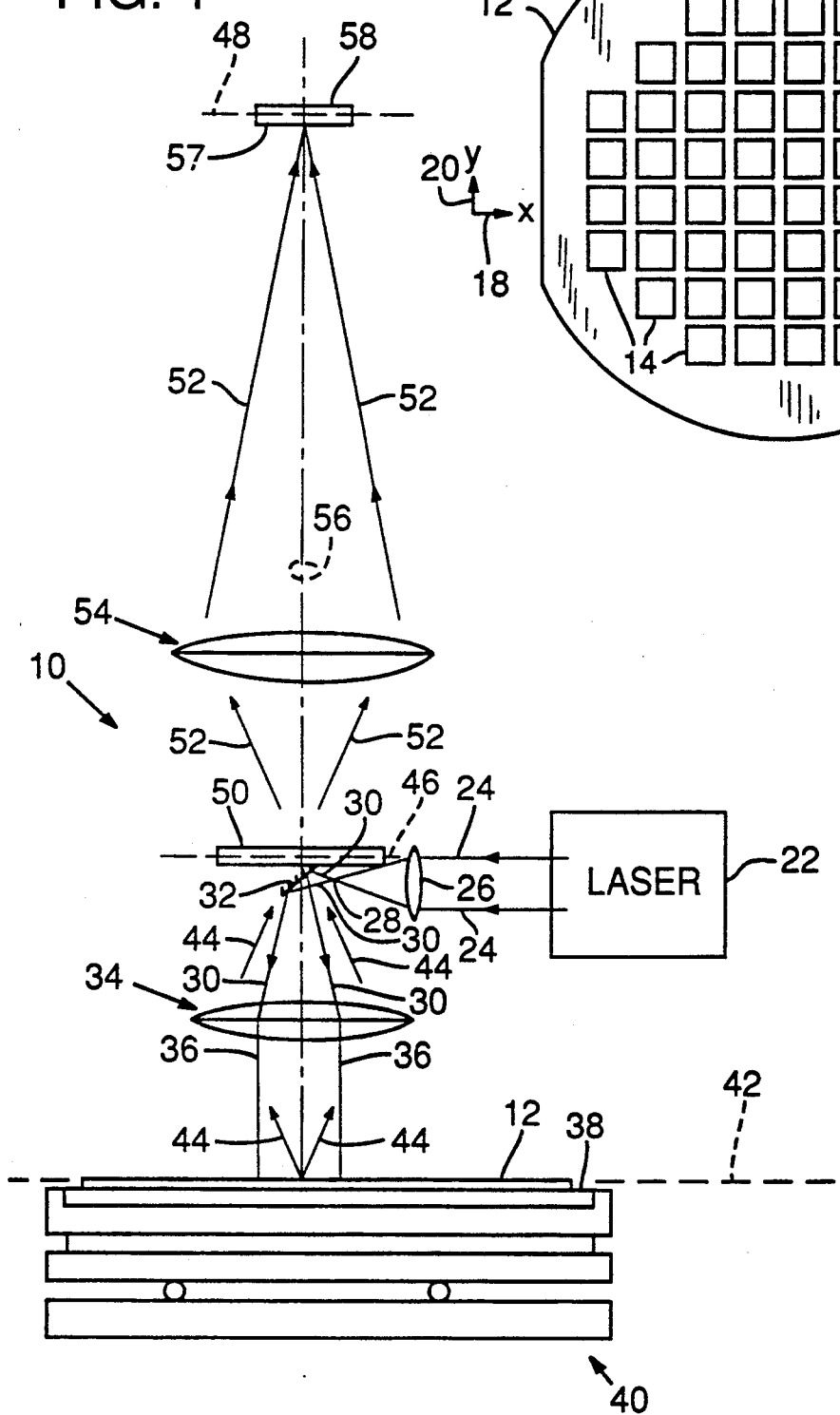

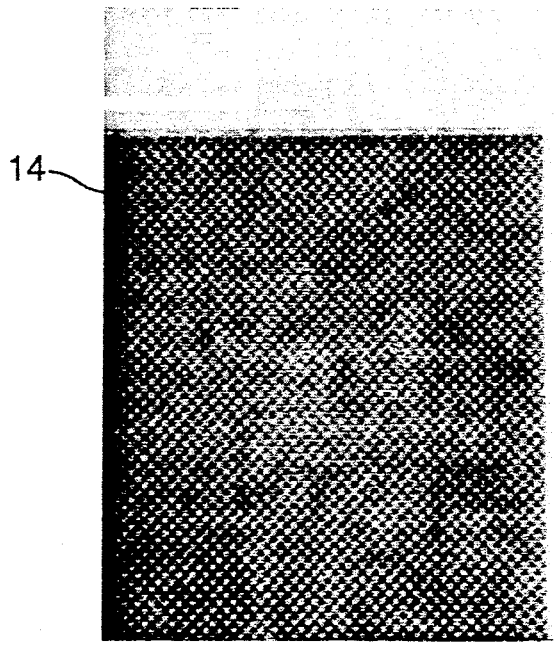
FIG. 3A
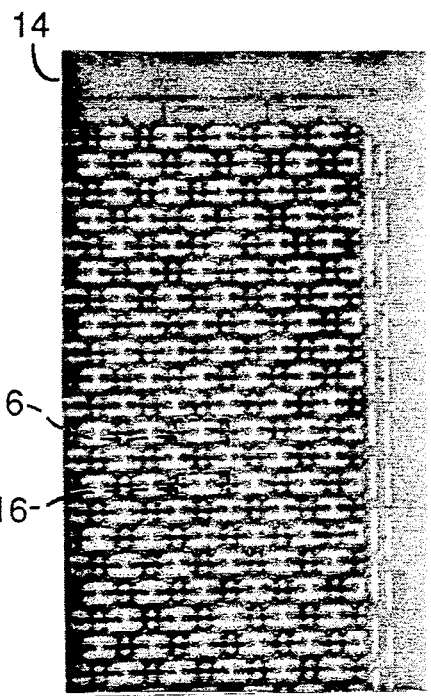
FIG. 3B
FIG. 3C
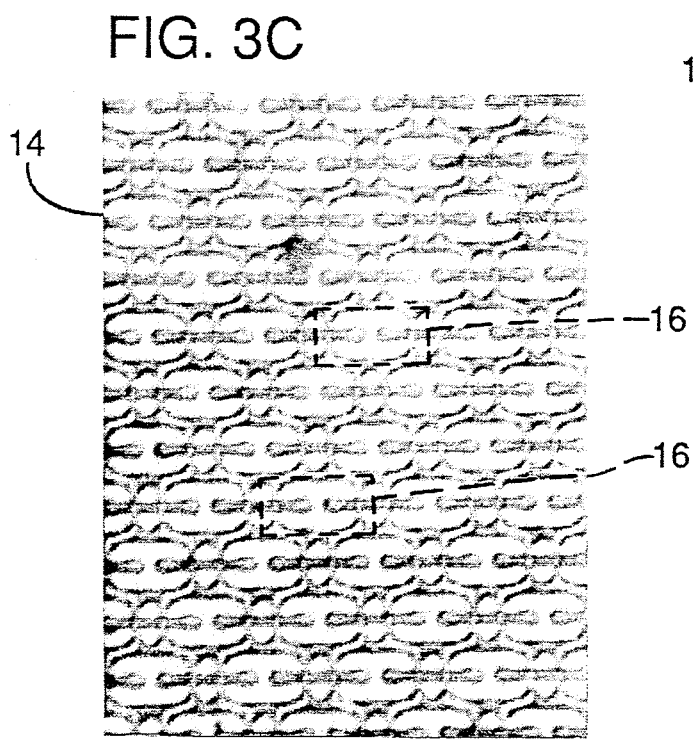

![5,172,000]

SPATIAL FILTER FOR OPTICALLY BASED DEFECT INSPECTION SYSTEM

TECHNICAL FIELD

The present invention relates to optically based specimen defect inspection systems and, in particular, to such systems that employ a spatial filter to block preselected spatial frequency components of a Fourier transform light pattern corresponding to an illuminated area of a specimen.

BACKGROUND OF THE INVENTION

U.S. Pat. No. 4,806,774 of Lin et al. describes an optical inspection system for detecting nonperiodic pattern defects in a patterned specimen, such as a wafer of the type employed in the large-scale manufacture of semiconductor devices and integrated circuits. The specimen includes many redundant circuit patterns. The inspection system employs a Fourier transform lens positioned along a system optic axis to produce a light pattern corresponding to the Fourier transform spatial frequency components of an illuminated area of the specimen wafer. A spatial filter positioned along the system optic axis intercepts the light pattern and cooperates with an inverse Fourier transform lens to produce an image pattern of nonperiodic defects located in the illuminated area of the wafer.

The spatial filter comprises a two-dimensional Fourier transform pattern of opaque and light-transmitting regions representing a substantially error-free wafer against which the specimen wafer is compared. The spatial filter may be fabricated by exposing a recording medium, such as a photographic plate, to light diffracted primarily by the illuminated redundant circuit patterns on the specimen wafer. The spatial frequency components corresponding to an error-free wafer are blocked by the opaque regions of the spatial filter, and the spatial frequency components corresponding to the defects in the specimen wafer are largely transmitted through the light-transmitting regions of the spatial filter to be processed for error detection.

Spatial filters employed in such a system suffer from at least three disadvantages. First, each filter employed in these systems corresponds only to a specific photomask configuration. As a result, a new filter must be manufactured for each wafer pattern to be inspected. Second, photographic or theory-based processes for manufacturing the spatial filters are relatively slow and limit the rate at which inspections may be performed. Third, replenishment of the materials for forming a spatial filter for each configuration increases the operating costs of the inspection system.

SUMMARY OF THE INVENTION

An object of the present invention is, therefore, to provide a spatial filter in an optically based specimen defect inspection system used in the manufacture of microcircuits.

Another object of this invention is to provide such a filter that can be used to inspect a number of different specimens.

A further object of this invention is to provide in an inspection system such a filter that facilitates a relatively high inspection rate.

Still another object of this invention is to provide such a filter that reduces the operating costs of an inspection system.

In a preferred embodiment, a spatial filter of the present invention is incorporated in a defect inspection system that operates under the principles of Fourier optics as described above with reference to U.S. Pat. No. 4,806,774 of Lin et al. The design of the spatial filter facilitates its use in the inspection of a number of specimens whose redundant pattern structures or "unit cell" patterns have different configurations within a specified range of sizes.

The spatial filter includes an array of multiple substantially parallel opaque stripes formed on a substantially transparent substrate. The stripes are of increasing widths as a function of their distances from a center stripe whose center line defines an axis of symmetry. The center stripe corresponds to the zero diffraction order of the Fourier transform pattern produced by the Fourier transform lens. The stripe widths vary in part in proportion to the range of unit cell dimensions that the spatial filter can cover. The stripe widths increase as a function of increasing order of diffraction. Adjacent stripes on either side of the axis of symmetry are spaced apart by center-to-center distances corresponding to diffraction orders of the Fourier transform pattern. The distances are typically integral multiples of the distance between the zero and first order diffraction patterns.

A spatial filter corresponds, therefore, primarily to unit cell dimensions of a specified range of sizes and is affected only to a lesser degree by the shapes of the circuit patterns within the unit cell. Accordingly, an inspection system may be provided with a library of spatial filters of the above-described type covering circuit patterns within different specified ranges of unit cell dimensions.

In a first preferred embodiment, each of the spatial filters in the library is an assembly of three glass plates including a photographic plate sandwiched between two outer plates. The outer plates eliminate wavefront distortion created by surface irregularities of the photographic plate. Small amounts of wavefront distortion could significantly affect the performance of the optical system, which operates with a high degree of resolution.

In a second preferred embodiment, the spatial filters constituting the library are formed on photographic film that is stored on a spool in a film storage cartridge. The film is immersed in a fluid whose index of refraction is matched to that of the film to prevent wavefront distortion. The fluid and a selected filter on the film are captured between two substantially parallel, optically flat windows that form an optical gate. The index-matching fluid eliminates a change in the index of refraction at the surface of the film, thereby allowing light to cross the surface without being distorted by irregularities therein.

In a third preferred embodiment, each of the spatial filters in the library includes a pattern of stripes that are formed of chrome-on-glass substrate. A robotic handler transfers a selected one of the spatial filters from a storage tray to the appropriate location along the optic axis of the inspection system.

The library of spatial filters eliminates the requirement that a different spatial filter be manufactured for each circuit pattern configuration. As a result, the inspection system can operate at a relatively high inspection rate because customized spatial filters need not be used. Moreover, elimination of a need to manufacture customized spatial filters reduces the operating costs of the inspection system.

Additional objects and advantages of the present invention will be apparent from the following detailed description of preferred embodiments thereof, which proceeds with reference to the accompanying drawings.

BRIEF DESCRIPTION OF THE DRAWINGS

FIG. 1 is a schematic diagram of the optical components of a defect inspection system employing a spatial filter of the present invention.

FIG. 2 is diagram of a semiconductor wafer comprising a regular array of normally identical dies of the type suitable for defect inspection by the system of FIG. 1.

FIGS. 3A-3C are photographs of an exemplary single die of the semiconductor wafer of FIG. 2, showing highly redundant unit cell circuit patterns for consecutively increasing magnifications.

DETAILED DESCRIPTION OF PREFERRED EMBODIMENTS

Figure 4:
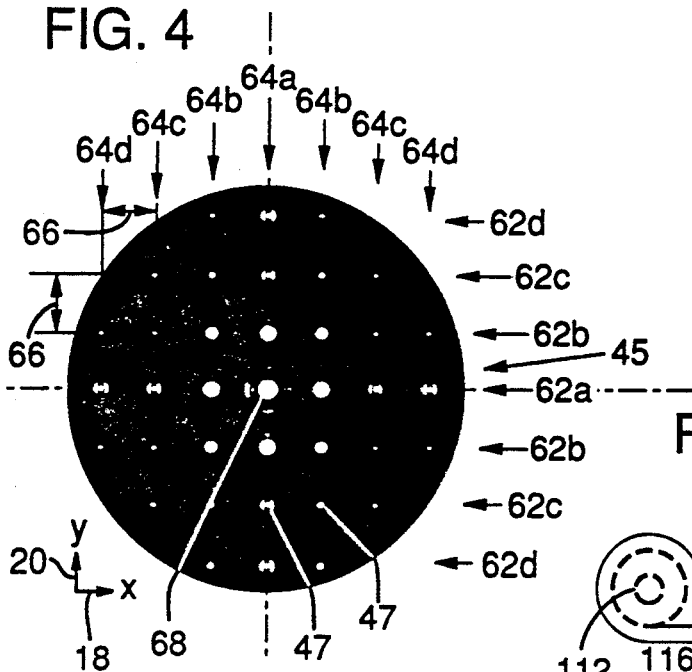
FIG. 4 is a photograph of an exemplary light pattern formed at the Fourier transform plane of the defect inspection system of FIG. 1.

FIG. 1 is a schematic diagram of an optical defect inspection system 10 that is designed to detect semiconductor wafer nonperiodic defects having a diameter of about one-quarter micron or larger in the presence of a periodic structure comprising many redundant circuit patterns. FIG. 2 is a diagram of a semiconductor wafer 12 of the type inspection system 10 is designed to inspect for defects. Wafer 12 includes a regular array of normally identical dies 14 of which each has at least about twenty redundant unit cells or circuit patterns 16 (FIGS. 3B and 3C) positioned along the directions of an X-axis 18 and a Y-axis 20. Each die 14 is typically of square shape with sides of about 3 millimeters.

FIGS. 3A-3C are photographs of an exemplary single die 14 showing highly repetitive circuit patterns 16 within the die for consecutively increasing magnifications. Although they are of rectangular shape as shown in FIGS. 3A-3C, circuit patterns 16 are assumed for purposes of simplifying the following discussion to be of square shape with sides of about 50 microns in length.

With reference to FIG. 1, inspection system 10 includes a laser source 22 that provides a nearly collimated beam of 442.5 nanometer monochromatic light rays 24 that strike a lens 26 that converges the light rays to a point 28 located in the back focal plane of lens 26. The light rays 30 diverge from focal point 28 to strike a small mirror 32 that is positioned a short distance from focal point 28 to reflect a relatively narrow circular beam of light toward a Fourier transform lens section 34, which is shown in FIG. 1 as a single element but which is implemented in five lens elements as described in U.S. Pat. No. 4,806,774 of Lin et al. Mirror 32 obscures a small region in the center of the Fourier transform plane defined by lens section 34. The size of the obscured region is sufficiently small so that defect information, which is located everywhere in the Fourier transform plane, is only insignificantly blocked by mirror 32.

The effective center of Fourier transform lens section 34 is positioned a distance of slightly less than one focal length away from mirror 32 to provide collimated light rays 36 that strike the patterned surface of wafer 12. Wafer 12 is mounted in a chuck 38 that constitutes part of a two-dimensional translation stage 40. Wafer 12 is positioned in the object or front focal plane 42 of lens section 34, and the collimated light rays 36 illuminate the patterned surface of wafer 12. The collimated light rays 36 illuminate a 20 millimeter diameter area of the surface of wafer 12. The light rays 44 reflected from and diffracted by the illuminated area of wafer 12 pass through lens section 34 and form a corresponding Fourier transform pattern 45 (FIG. 4) in the back focal plane 46 of lens section 34.

Fourier transform pattern 45 comprises spots 47 of light that are distributed in a predictable manner as a rectangular array in back focal plane 46. The 20 millimeter diameter illuminated area of wafer 12 provides a Fourier transform pattern of sufficient accuracy because it is formed from many redundant circuit patterns. The design of lens section 34 is, however, such that it has only a 3 millimeter object field diameter to form in the image plane 48 an essentially aberration-free image of defects in the semiconductor wafer. An entire die can be inspected for defects because translation stage 40 moves the die through the illuminated area. Therefore, a relatively large area of wafer 12 is illuminated to develop an accurate Fourier transform pattern of the redundant circuit patterns, but a lens of relatively small object field diameter collects the light diffracted by the illuminated area to minimize the introduction of aberrations into the Fourier transform pattern as it is formed.

A previously fabricated spatial filter 50 of the present invention is positioned in the back focal plane 46 of lens section 34. Spatial filter 50 blocks the spatial frequencies of the error-free Fourier transform of the illuminated circuit patterns 16 of dies 14 but allows the passage of light originating from possible nonperiodic defects in such dies. The defect-carrying light rays 52 not blocked by spatial filter 50 strike an inverse Fourier transform lens section 54, which is shown schematically as a single lens but includes four lens elements as described in U.S. Pat. No. 4,806,774 of Lin et al. Lens section 54 performs the inverse Fourier transform on the filtered light pattern of the illuminated wafer circuit patterns 16. Lens section 54 may be positioned a distance of one focal length away from back focal plane 46 of lens section 34. The elements of lens sections 34 and 54 are aligned along the same optic axis 56, and translation stage 40 moves circuit patterns 16 across optic axis 56 to form on a light-sensitive surface 57 of a photodetector array 58 images of the nonperiodic defects in circuit patterns 16.

FIG. 4 is a photograph of an exemplary Fourier transform pattern 45 that is formed in back focal plane 46 of Fourier transform lens section 34 and includes a regular array of spots 47 of light mutually spaced apart by a distance corresponding to the size of the unit cells 16 of wafer 12. The array defines a grid of imaginary intersecting horizontal rows 62a, 62b, 62c, and 62d and vertical columns 64a, 64b, 64c, and 64d that interconnect adjacent light spots 47. The distances 66 between the centers of next adjacent spots in any row or in any column are the same. Light spots 47 lying along row 62a and column 64a define, respectively, a horizontal axis and a vertical axis that include zero diffraction order light spots. The horizontal axis and vertical axis are aligned with the X-axis 18 and Y-axis 20, which are defined in FIG. 1 relative to the orientation of wafer 12 from which light spots 47 are produced. The rows and columns of light spots 47 located at increasing distances from horizontal axis 62a and vertical axis 64a include light spots 47 of increasing diffraction order. More specifically, rows 62b and columns 64b include first order light spots; rows 62c and columns 64c include second order light spots; and rows 62d and columns 64d include third order light spots.

FIG. 4 shows that the center spot 68 has the largest diameter and is located at the intersection of horizontal axis 62a and vertical axis 64a. The sizes of light spots 47 decrease with increasing diffraction order and with increasing distance from center spot 68.

Figure 5:
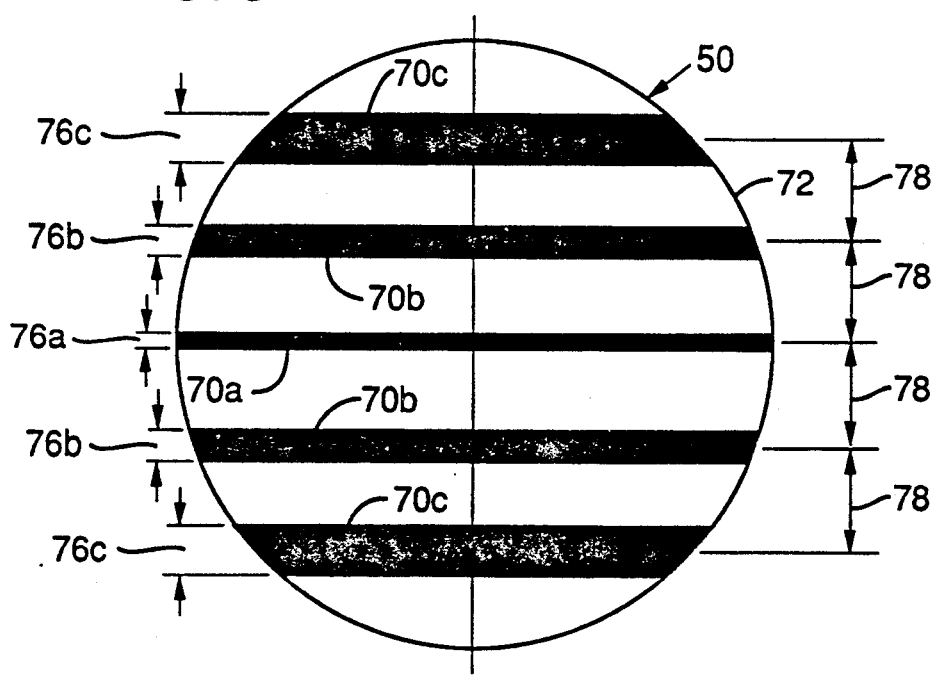
FIG. 5 is a diagram of a spatial filter of the present invention.

FIG. 5 is an enlarged diagram of a preferred design of spatial filter 50, which is adapted for unit cell circuit patterns 16 of sizes within a given range and is one example of a number of spatial filters included in a spatial filter library (not shown). Spatial filter 50 includes an array of multiple parallel opaque stripes 70a, 70b, and 70c of different widths positioned on a transparent substrate 72.

Stripes 70a–70c are positioned on spatial filter 50 to block the transmission of light from light spots 47 in the respective rows 62a–62c of Fourier transform pattern 45. (A pair of stripes blocking light from rows 62d have been omitted for purposes of clarity only.) The widths of and the distances separating next adjacent stripes for each filter in the spatial filter library are determined by several factors, which relate in part to the unit cell size. The following relationships hold for a particular filter design covering a specified range of unit cell sizes.

First, the center-to-center distances separating adjacent stripes depend on the unit cell size. This is so because light spots 47 produced from unit cells 16 of decreasing size are separated by increasing distances.

Second, center stripe 70a is of a particular stripe width 76a, and nonzero order stripes 70b and 70c are of respective increasing stripe widths 76b and 76c for each increasing diffraction order. The width 76b of first nonzero order stripes 70b is, in part, proportional to the range of unit cell sizes to be covered by the filter. The width 76c of second nonzero order stripes 70c is twice that of width 76b of first order stripes 70b. The widths of higher order stripes are, in general, set in accordance with the expression $$h_n = n \cdot h_1,$$

where n is the diffraction order, $h_n$ is the width of an nth order stripe, and $h_1$ is the width of the first order stripe. It follows, therefore, that an increase in the range of unit cell sizes requires an increase in stripe width.

Third, as indicated in FIG. 4, light spots 47 are of different sizes, depending on their proximity to center spot 68.

In summary, the stripe widths of spatial filter 50 are determined by the range of unit cell sizes and by the range of spot sizes in the Fourier transform patterns covered by spatial filter 50.

The center-to-center spacing distance 78 between adjacent stripes of a spatial filter 50 covering a range of unit cell sizes is preferably the same for all stripes. It will be appreciated that, although width 76a of the center or zero order stripe 70a is sufficient to block light coming from the largest light spots 47 in Fourier transform pattern 45, zero order stripe 70a is the narrowest stripe shown in FIG. 5.

A strategy for determining an appropriate range of unit cell sizes is to select a particular initial size of unit cell 16, which sets the upper boundary for the range, and increase the range of unit cell sizes until a specified minimum transmission ratio for the filter is reached. The transmission ratio of spatial filter 50 is defined as the area between the filter stripes divided by the total area of the circle. In a preferred embodiment, the minimum transmission ratio is 0.45. As was stated above, increasing the unit cell size increases the stripe widths and thereby reduces the light transmissive area of spatial filter 50. Therefore, the unit cell size that gives stripes whose total area equals 55 percent of the total circular area of spatial filter 50 represents the lower boundary of the range of unit cell sizes.

This strategy not only sets the unit cell size range for the filter but also sets the starting point, i.e, upper boundary, of the next highest successive order spatial filter in the library. To ensure filtering over adjacent spatial frequency bands, the frequency intervals covered by spatial filters in next successive order must be closed and overlap at the lower boundary of the lower order filter. (The term "adjacent spatial frequency bands" as used in this context refers to the fundamental spatial frequency for a given unit periodicity.)

Figure 6:
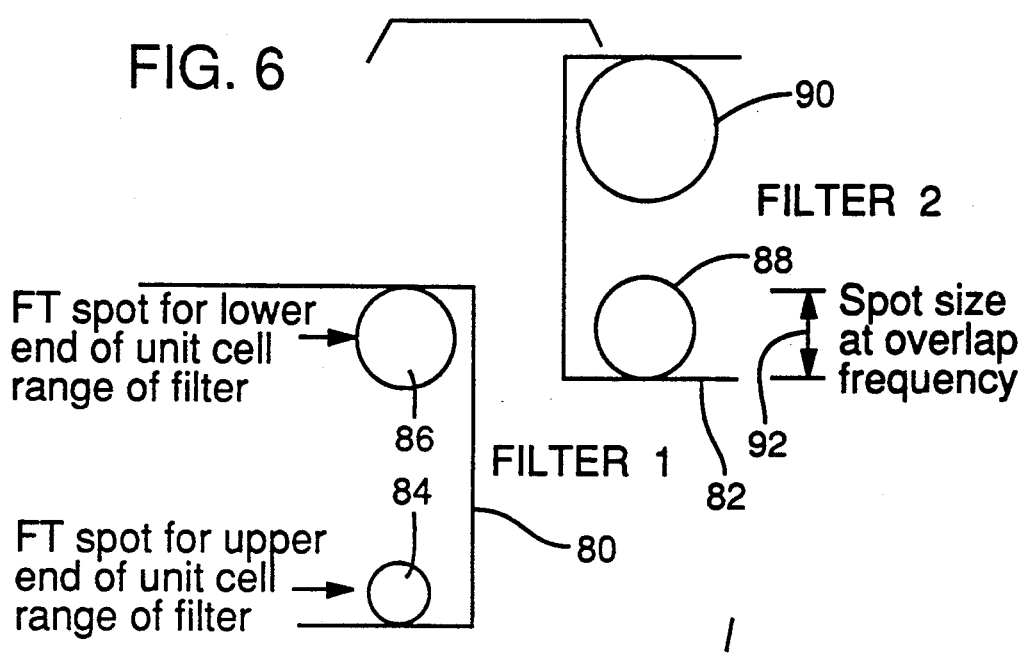
FIG. 6 is a diagram showing the overlap of the spatial frequency end points of two spatial filters in successive order in a spatial filter library formed in accordance with the present invention.

FIG. 6 is a diagram showing the overlap of the upper boundary points of successive filters 80 and 82 in the library. Filter 80 includes spots 84 and 86 representing, respectively, the upper and lower boundaries of the unit cell size range. Filter 82 includes spots 88 and 90 representing, respectively, the upper and lower boundaries of the unit cell size range. Filter 82 overlaps filter 80 only at one point, which is represented by spot 88, in the frequency domain. Spot 88 has a spot diameter 92 that represents the overlap frequency. The reason for a finite spatial overlap, which is equal to the spot diameter at the single overlap frequency, is that there is a finite object field for the Fourier transform and a practical limit of lens resolution. (In the limit of infinite object field and lens resolution, the spatial overlap shown in FIG. 6 reduces to a single point overlap in the frequency domain.)

Figure 7:
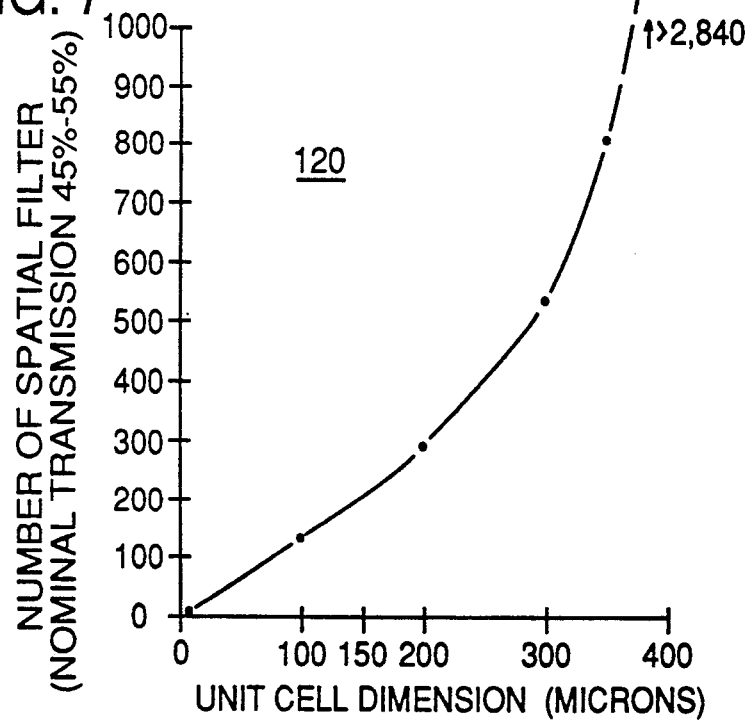
FIG. 7 is a graph showing the relationship between the number of spatial filters of the type shown in FIG. 5 required to cover a unit cell circuit pattern of a given maximum dimension.

FIG. 7 is a graph 120 showing the number of spatial filters 50 required in a spatial filter library for square and rectangular unit cell circuit patterns 16 of different sizes. For example, a spatial filter library covering unit cell circuit pattern sizes of between 250 microns and 400 microns requires approximately 2440 filters, which is calculated as the difference between the number of filters required for unit cell circuit patterns 16 of up to 400 microns in size (i.e., 2840 filters) and the number of filters required for unit cell circuit patterns 16 of up to 250 microns in size (i.e., 400 filters).

Figure 8:
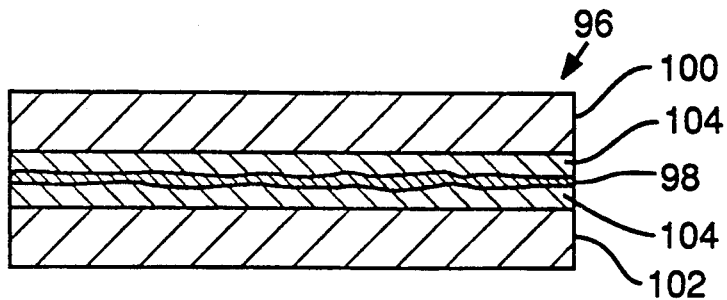
FIG. 8 is a diagram showing a side view of one of a set of spatial filters of a preferred type in a spatial filter library formed in accordance with the present invention.

FIG. 8 shows a first preferred embodiment in which each of spatial filters 50 in the library is an assembly 96 of three glass plates including a photographic plate 98 sandwiched between two outer glass plates 100 and 102. Photographic plate 98 is shown with an exaggerated curved surface profile to indicate a nonuniform surface flatness for both sides of the plate. The nonuniform surface flatness introduces wavefront phase distortion to incident light. To minimize such phase distortion, outer plates 100 and 102 with highly uniform optically flat surfaces are positioned on either side surface of plate 98. Since the glass material forming plates 98, 100, and 102 have about the same index of refraction, index matching glue layers 104 deposited between the inner surfaces of outer plates 100 and 102 and the outer surfaces of photographic plate 98 holds assembly 96 together, compensating for surface flatness differences and providing a uniform index of refraction for the assembly.

Figure 9:
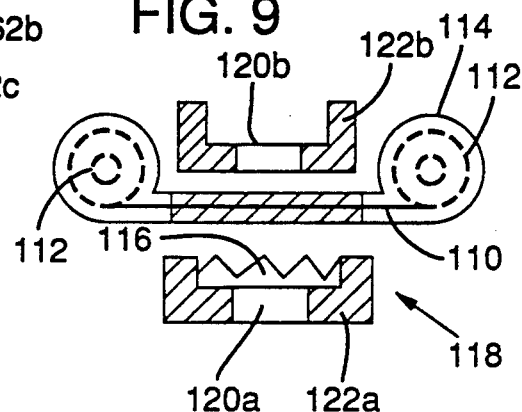
FIG. 9 is a diagrammatic side view, with portions shown in section, of an optical gate in which a preferred spatial filter library is contained on a roll of photographic film.

FIG. 9 shows a second preferred embodiment in which a library of spatial filters 50 is formed on a strip of photographic film 110 that is stored on a pair of spools 112 contained within a film storage cartridge 114. The surface of the film 110 typically does not have sufficient flatness to minimize the amount of phase distortion created by the spatial filter. To minimize such phase distortion, film 110 is immersed in an index matching fluid 116 that is captured within an optical gate 118, the fluid 116 having an index of refraction matched to that of film 110. Optical gate 118 has two substantially parallel, optically flat windows 120a and 120b supported by respective window assemblies 122a and 122b between which fluid 116 is captured.

Window assemblies 122a and 122b are separable so that a spatial filter 50 can be accessed by a computer-controlled motor (not shown) driving one of the spools 112 in film storage cartridge 114. Once a selected spatial filter 50 on film 110 is accessed and aligned with windows 120a and 120b, window assemblies 122a and 122b are moved close together to secure them against the opposite sides of film 110 and thereby immerse film 110 in index-matching fluid 116. Alternatively, film cartridge 114 may be permanently immersed within index matching fluid 116 in a fixedly closed optical gate (not shown). Although of a configuration simpler than that of optical gate 118, a closed optical gate suffers from the disadvantages of generating relatively large amounts of heat and turbulence in the index matching fluid during the selection of a particular spatial filter 50.

In a third preferred embodiment, each of the spatial filters in the library includes a pattern of stripes 70a-70c that are formed of chrome-on-optically flat glass substrate. A robotic handler (not shown) transfers a selected one of spatial filters 50 from a storage tray to the appropriate location on optic axis 56. The spatial filters 50 may be manufactured by etching a chromium film from a glass substrate by means of a conventional photoresist lithography process. Such filters typically have sufficient flatness to satisfy the requisite minimum phase distortion criterion.

It will be obvious to those having skill in the art that many changes may be made in the above-described details of the preferred embodiment of the present invention without departing from the underlying principles thereof. For example, certain specimens such as liquid crystal display panels have less unit cell pattern deviation among different types of liquid crystal display panels. As a consequence, the spatial filter stripe widths could be predicted with greater accuracy. It is possible in such instances that the optimum stripe width distribution may differ from the above-described formulation of increasing stripe width as a function of increasing diffraction order for multiple integrated circuit dies having redundant die circuit patterns. The scope of the present invention should, therefore, be determined only by the following claims.

We claim:

1. In an imaging system for detecting nonperiodic defects in a specimen having a repetitive unit cell pattern, the system including a lens arrangement positioned along an optic axis to form a pattern of light diffracted by the specimen, the light pattern including spots of light representing the spatial frequency spectrum of the repetitive unit cell pattern of the specimen, the light spots being arranged in rows and being mutually spaced apart by distances corresponding to the size of the repetitive unit cell pattern, a spatial filter for receiving and blocking the light spots of multiple specimens whose repetitive unit cell patterns vary over a range of sizes, comprising:

an array of plural substantially parallel opaque stripes positioned on a substantially transparent substrate, the opaque stripes including a center stripe and a pair of stripes positioned on either side of the center stripe, the center stripe having a center stripe width and the pair of stripes having a first stripe width that is greater than the center stripe width, the stripes being spaced apart by distances corresponding to the size of the repetitive unit cell pattern.

2. The filter of claim 1 in which next adjacent stripes are separated by center-to-center distances and the pair of stripes are separated from the center stripe by equal center-to-center distances.

3. The filter of claim 1 in which the pair of stripes define a first pair, and further comprising a second pair of stripes separated from each other by the center stripe and the first pair of stripes, the second pair of stripes having a second stripe width that is greater than the first stripe width.

4. The filter of claim 3 in which the second stripe width is twice the first stripe width.

5. The filter of claim 1 in which the substantially transparent substrate includes a photographic film.

6. The filter of claim 5 in which the photographic film is supported between a pair of optical windows and in contact with a fluid having an index of refraction similar to that of the photographic film, the optical windows being aligned with the optic axis.

7. In an imaging system for detecting nonperiodic defects in a specimen having a repetitive unit cell pattern, the system including a lens arrangement positioned along an optic axis to form a pattern of light diffracted by the specimen, the light pattern including spots of light representing the spatial frequency spectrum of the repetitive unit cell pattern of the specimen, the light spots being arranged in rows and columns and being mutually spaced-apart by distances corresponding to the size of the repetitive unit cell pattern, a library of spatial filters each of which is adapted to receive and block the spatial frequency light spots of multiple specimens whose repetitive unit cell patterns vary over a range of sizes comprising:

a first spatial filter having a first set of plural nonintersecting opaque stripes spaced apart on a substantially transparent substrate, the opaque stripes having stripe widths corresponding to the orders of diffraction of the spatial frequency components formed from specimens having unit cell patterns of sizes within the first range of sizes; and a second spatial filter having a second set of plural nonintersecting opaque stripes spaced apart on a substantially transparent substrate, the opaque stripes having stripe widths corresponding to the plural orders of diffraction of the spatial frequency components formed from specimens having unit cell patterns of sizes within a second range of sizes that is substantially nonoverlapping of the first range of sizes.

8. The filter library of claim 7 in which the nonintersecting opaque stripes of each of the first and second spatial filters are in generally parallel orientation.

9. The filter library of claim 7 in which each of the first and second spatial filters includes a center stripe and a first pair of stripes positioned generally parallel to and on either side of the center stripe.

10. The method of claim 9 in which the center stripe is of lesser thickness than either one of the first pair of stripes.

11. The filter library of claim 9 in which the first pair of stripes is separated from the center stripe by equal center-to-center distances.

12. The filter library of claim 7 in which each of the first and second filters includes a center stripe of predetermined width, the width of the center stripe of the first filter differing from that of the second filter.

13. In an imaging system for detecting nonperiodic defects in a specimen having a repetitive unit cell pattern, the system including a lens arrangement positioned along an optic axis to form a pattern of light diffracted by the specimen, the light pattern including spots of light representing the spatial frequency spectrum of the periodic pattern of the specimen, the light spots being arranged in rows and being mutually spaced apart by distances corresponding to the size of the repetitive unit cell pattern, a method of providing a spatial filter for receiving and blocking the light spots of multiple specimens whose repetitive unit cell patterns vary over a range of sizes, comprising:

generating a spatial filter having multiple nonintersecting, spaced-apart stripes of different widths corresponding to the range of unit cell sizes of the specimens.

14. The method of claim 13 in which the spatial filter includes a center stripe and a first pair of stripes positioned generally parallel to and on either side of the center stripe.

15. The method of claim 14 in which the center stripe is of lesser thickness than either one of the first pair of stripes.

16. The method of claim 14 in which the first pair of stripes is separated from the center stripe by center-to-center distances of the same amount.

17. The method of claim 13 in which the stripes are in generally parallel orientation.

* * * * *